United States Patent [19]

Nichols et al.

[11] Patent Number: 5,420,134
[45] Date of Patent: May 30, 1995

[54] SUBSTITUTED HEXAHYDROBENZO[A]PHENANTHRIDINES

[75] Inventors: David E. Nichols, West Lafayette, Ind.; Richard B. Mailman, Chapel Hill, N.C.

[73] Assignees: Purdue Research Foundation, West Lafayette, Ind.; University of North Carolina at Chapel Hill, Chapel Hill, N.C.

[21] Appl. No.: 129,810

[22] Filed: Sep. 30, 1993

Related U.S. Application Data

[63] Continuation of Ser. No. 887,692, May 26, 1992, abandoned.

[51] Int. Cl.$^6$ .................... C07D 215/58; A61K 31/44
[52] U.S. Cl. ...................................... 514/280; 514/284; 546/48; 546/61
[58] Field of Search .................... 546/48, 61; 514/280, 514/284

[56] References Cited

U.S. PATENT DOCUMENTS

| | | | |
|---|---|---|---|
| 3,912,740 | 10/1975 | Zee-Cheng et al. | 260/286 |
| 3,939,165 | 2/1976 | Schwan | 546/61 |
| 4,737,503 | 4/1988 | Sakamoto et al. | 514/279 |
| 5,047,536 | 9/1991 | Nichols | 546/61 |

FOREIGN PATENT DOCUMENTS

PCT/US91/-
06440 9/1991 WIPO.

OTHER PUBLICATIONS

Chemical Abstracts CA117: 26359 (1991).
Chemical Abstracts CA116: 51351 (1991).
Chemical Abstracts CA115: 256024 (1990).
Chemical Abstracts CA115: 85324 (1990).
Chemical Abstracts CA115: 717 (1990).
Chemical Abstracts CA112: 235152 (1990).
Chemical Abstracts CA111: 187294 (1989).
Chemical Abstracts CA83: 141745 (1975).

Gordon N. Walker, *Hypotensive Methoxyisoquinolines*, JACS, vol. 76, pp. 3999–4003 (1954).

G. Laus, D. Tourwé, G. Van Binst, *Benzo–and Indoloquinolizidine Derivatives XIX. The Synthesis and Pharmacological Activity of Some Quinolizidine Derivatives, Analogues of Butaclamol*, Heterocycles, vol. 22, No. 2, pp. 311–331 (1984).

Robert Mack Riggs, *Studies Directed Toward the Design of Specific Dopamine D-1/DA-1 Agonists and Antagonists*, A Thesis Submitted to the Faculty of Purdue University, 1986.

(List continued on next page.)

*Primary Examiner*—Johann Richter
*Assistant Examiner*—Catherine S. Kilby Scalzo
*Attorney, Agent, or Firm*—Barnes & Thornburg

[57] ABSTRACT

Trans-hexahydrobenzo[a]phenanthridine of the formula

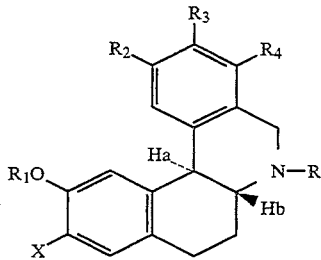

wherein R is hydrogen or $C_1$–$C_4$ alkyl; $R_1$ is hydrogen or a phenoxy protecting group, X is fluoro, chloro, bromo, iodo or a group of the formula —$OR_5$, and $R_2$, $R_3$, and $R_4$ are independently selected from the group consisting of hydrogen, $C_1$–$C_4$ alkyl, phenyl, fluoro, chloro, bromo, iodo, or a group —$OR_1$ provided that at least one of $R_2$, $R_3$, and $R_4$ are other than hydrogen, are novel ligands for dopamine receptors.

20 Claims, No Drawings

OTHER PUBLICATIONS

Chung-Chen Wei, Sidney Teitel, *Synthesis of a Benzo[a]Phenanthridine Isomeric With Apomorphine*, Heterocycles, vol. 8, pp. 97–102 (1977).

Sanji Hagishita, Motoo Shiro, Kaoru Kuriyama, *Synthesis and C.d. Spectra of 6,6a,7,11b–Tetrahydro–5H–indeno[2,1–c]–isoquinoline Derivatives*, J. Chem. Soc. Perkin Trans. 1, vol. 8, pp. 1655–1669 (1984).

William K. Brewster, et al., *trans–10,11–Dihydroxy–5,6,6a,7,8,12b–hexahydrobenzo[a]phenanthridine: A Highly Potent Selective Dopamine $D_1$ Full Agonist*, Journal of Medicinal Chemistry, vol. 33, No. 6, (1990).

M. K. Menon, W. G. Clark, J. G. Cannon, *Comparison of the Dopaminergic Effects of N–substituted Aporphines*, J. Pharm. Pharmac., Communications, vol. 28, pp. 778–781 (1976).

J. D. Kohli, *Dopamine Receptor Agonists and Antagonists*, Proc. West. Pharmacol. Soc., vol. 33, pp. 21–27 (1990).

SUBSTITUTED HEXAHYDROBENZO[A]PHENANTHRIDINES

This application is a continuation of Ser. No. 07/887,692, filed May 26, 1992, now abandoned.

FIELD OF INVENTION

This invention relates to novel ligands for dopamine receptors. More particularly, this invention is directed to certain substituted transhexahydrobenzo[a]phenanthridine compounds useful as dopamine-like agents or dopamine receptor blockers.

BACKGROUND AND SUMMARY OF THE INVENTION

Dopamine, a neurotransmitter in the central nervous system ("CNS"), has been implicated in numerous neurological disorders. For example, it has been hypothesized that excess stimulation of dopamine receptor subtypes may be linked to schizophrenia. Additionally, it is generally recognized that either excessive or insufficient functional dopaminergic activity in the central nervous system may cause hypertension, narcolepsy, and other behavioral, neurological, physiological, and movement disorders including Parkinson's disease, a chronic, progressive disease characterized by an inability to control the voluntary motor system.

It is generally accepted that there are at least two pharmacological subtypes of dopamine receptors (D-1 and D-2), each consisting of several molecular forms. While the physiological activities associated with the interaction with dopamine with those respective receptor subtypes are not fully understood, it is known that ligands exhibiting selectivity for activation/blockade with one or the other of the receptor subtypes produce more or less predictable, neuropharmacological results. CNS drugs exhibiting affinity for the dopamine receptors are generally classified not only by their receptor selectivity, but further by the character of their receptor interaction, i.e., by their agonist (receptor stimulating) or antagonist (receptor blocking) activity. More recently, it has been suggested that dopamine receptor ligands may further be characterized by selectivity for either presynaptic or postsynaptic receptors. As the neuropharmacological effects caused by association of selective ligands (agonist vs. antagonist) with specific receptor subtypes becomes better understood, drug researchers will be much better positioned to design CNS drugs targeting specific neurological or psychiatric disorders. Drugs with the ability to selectively block or stimulate D-1 or D-2 dopamine receptors are of significant interest in the CNS medical research community.

The present invention provides novel $C_2$, $C_3$, and/or $C_4$-substituted trans-5,6,6a, 7,8,12b-hexahydrobenzo[a]phenanthridines. They are related generally to the compounds described in co-owned U.S. Pat. No. 5,047,536, issued Sep. 10, 1991, including particularly the compound trans-10,11-dihydroxy-5,6,6a,7,8,12b-hexahydrobenzo[a]phenanthridine (dihydrexidine), a D-1 agonist which has been the subject of much study over the past several years. The biological activities of the present compounds vary significantly in their selectivity for the dopamine receptor subtypes, depending on the nature and positioning of the substituent groups. Substitution at the $C_2$, $C_3$, and/or $C_4$ position on the benzophenanthridine ring system has been found to provide a means for controlling receptor affinity and concomitantly receptor selectivity. Thus, for example, 2-methyldihydrexidine has D-1 potency and efficacy comparable to dihydrexidine, while it has a five fold enhanced selectivity for the D-1 receptor. In contrast, the compound 3-methyldihydrexidine while retaining potency and efficacy as dihydrexidine, has greater D-2 potency, making it less selective but able to activate better both types of receptors. Further, data on the present substituted hexahydrobenzo[a]phenanthridines suggest that the D-2 affinity is selective for postsynaptic dopamine D-2 receptors. It is anticipated that the present ligands will offer significant therapeutic benefit over compounds exhibiting presynaptic D-2 effects because they should evoke less neural accommodation of the dopamine neurons. The postsynaptic D-2 selectivity of dihydrexidine itself and the present 2-, 3-, and/or 4-substituted dihydrexidine compounds is without antecedent in the art.

The present compounds can be administered by oral or parenteral routes of administration in amounts effective to evoke therapeutic responses in patients suffering from, for example, hypertension, Parkinson's disease, attention deficit disorder, narcolepsy, schizophrenia, other psychiatric conditions, and other diseases deriving from central nervous system dysfunction.

Additional objects, and advantages of the invention will become apparent to those skilled in the art upon consideration of the following detailed description of preferred embodiments exemplifying the best mode of carrying out the invention.

DETAILED DESCRIPTION OF THE INVENTION

There is provided by this invention substituted hexahydrobenzo[a]phenanthridine compounds of the general formula

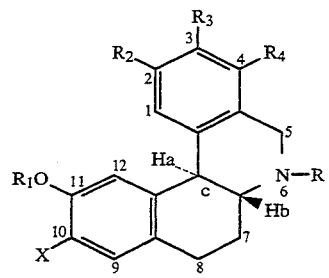

and pharmaceutically acceptable salts thereof, wherein $H_a$ and $H_b$ are trans across ring fusion bond c; R is hydrogen or $C_1$–$C_4$ alkyl; $R_1$ is hydrogen or a phenoxy protecting group; X is fluoro, chloro, bromo, or iodo, or a group of the formula —$OR_5$ wherein $R_5$ is hydrogen or a phenoxy protecting group, provided that when X is a group of the formula —$OR_5$, the groups $R_1$ and $R_5$ can be taken together to form a —$CH_2$— group, thus representing a methylenedioxy functional group bridging the C-10 and C-11 positions on the hexahyrobenzo[a]phenanthridine ring system (as labelled above in Formula I); and $R_2$, $R_3$, and $R_4$ are independently selected from the group consisting of hydrogen, $C_1$–$C_4$ alkyl, phenyl, fluoro, chloro, bromo, iodo, or a group —$OR_1$ wherein $R_1$ is as defined above, provided that at least one of $R_2$, $R_3$, and $R_4$ are other than hydrogen.

The term "$C_1$–$C_4$ alkyl" as used herein refers to branched or straight chain alkyl groups comprising one to four carbon atoms, including, but not limited to, methyl, ethyl, propyl, isopropyl, n-butyl, t-butyl and cyclopropylmethyl.

The term "pharmaceutically acceptable salts" refers to those salts which are suitable for use in contact with the tissues of humans and lower animals without undue toxicity, irritation, allergic response and the like, and are commensurate with a reasonable benefit/risk ratio. Pharmaceutically acceptable salts are well known in the art. The salts can be prepared according to conventional methods in situ during the final isolation and purification of the compounds, or separately by reacting the free base with a suitable organic acid.

The term "phenoxy protecting group" as used herein refers to substituents on the phenolic oxygen which prevent undesired reactions and degradations during synthesis and which can be removed later without effect on other functional groups on the molecule. Such protecting groups and the methods for their application and removal are well known in the art. They include ethers, such as methyl, isopropyl, t-butyl, cyclopropylmethyl, cyclohexyl, allyl ethers and the like; alkoxyalkyl ethers such as methoxymethyl or methoxyethoxymethyl ethers and the like; alkylthioalkyl ethers such a methylthiomethyl ethers; tetrahydropyranyl ethers; arylalkyl ethers such as benzyl, o-nitrobenzyl, p-methoxybenzyl, 9-anthrylmethyl, 4-picolyl ethers and the like; trialkylsilyl ethers such as trimethylsilyl, triethylsilyl, t-butyldimethylsilyl, t-butyldiphenylsilyl ethers and the like; alkyl and aryl esters such as acetates, propionates, n-butyrates, isobutyrates, trimethylacetates, benzoates and the like; carbonates such as methyl, ethyl, 2,2,2-trichloroethyl, 2-trimethylsilylethyl, vinyl, benzyl and the like; and carbamates such as methyl, isobutyl, phenyl, benzyl, dimethyl and the like.

The term "$C_1$-$C_4$ alkoxy" as used herein refers to branched or straight chain alkyl groups comprising one to four carbon atoms bonded through an oxygen atom, including, but not limited to, methoxy, ethoxy and t-butoxy.

The compounds of this invention are prepared using the same preparative chemical steps described for the preparation of the hexahydrobenzo[a]phenanthridine compounds described and claimed in U.S. Pat. No. 5,047,536, issued Sep. 10, 1991, which is expressly incorporated herein by reference. The present compounds are prepared using the chemical reactions depicted in the reaction scheme illustrated in FIGS. 1 and 2 of U.S. Pat. No. 5,047,536 using the appropriately substituted benzoic acid acylating agent starting material instead of the benzoyl chloride reagent used in the initial reaction step. Thus, for example, use of 4-methylbenzoyl chloride will yield a 2-methyl hexahydrobenzo[a]phenanthridine compound of the present invention.

EXAMPLE 1

2-(N-benzyl-N-4-methylbenzoyl)-6,7-dimethoxy-3,4-dihydro-2-naphthylamine. To a solution of 4.015 g (19.5 mmol) of 6,7-dimethoxy-β-tetralone in 100 ml of toluene was added 2.139 g (1.025 equiv.) of benzylamine. The reaction was heated at reflux overnight under $N_2$ with continuous water removal. The reaction was cooled and the solvent was removed by rotary vacuum evaporation to yield the crude N-benzyl enamine as a brown oil.

Meanwhile, the 4-methylbenzoyl chloride acylating agent was prepared by suspending 3.314 g (24.3 mmol) of p-toluic acid in 200 ml benzene. To this solution was added 2.0 equiv. (4.25 ml) of oxalyl chloride, dropwise via a pressure-equalizing dropping funnel at 0° C. DMF (2-3 drops) was added to the reaction mixture catalytically and the ice bath was removed. The progress of the reaction was monitored via infrared spectroscopy. The solvent was removed by rotary vacuum evaporation and the residual oil was pumped down under high vacuum overnight.

The crude N-benzyl enamine residue was dissolved in 100 ml of $CH_2Cl_2$, and to this solution was added 2.02 g (19.96 mmol) of triethylamine at 0° C. 4-methylbenzoyl chloride (3.087 g, 19.96 mmol) was dissolved in 20 ml $CH_2$-$Cl_2$ and this solution was added dropwise to the cold, stirring N-benzyl enamine solution. The reaction was allowed to warm to room temperature and was left to stir under $N_2$ overnight. The reaction mixture was washed successively with 2×30 ml of 5% aqueous HCl, 2×30 ml of saturated sodium bicarbonate solution, saturated NaCl solution, and was dried over $MgSO_4$. After filtration, the filtrate was concentrated under vacuum. Crystallization from diethyl ether gave 5.575 g (69.3%) of the enamide mp 96°-98° C. CIMS (isobutane); M+1 414; $^1$H-NMR ($CDCl_3$); δ7.59 (d, 2, ArH), 7.46 (m, 3, ArH), 7.35 (m, 3, ArH), 7.20 (d, 2, ArH), 6.60 (s, 1, ArH), 6.45 (s, 1, ArH), 6.18 (s, 1, ArCH), 5.01 (s, 2, $ArCH_2N$), 3.80 (S, 3, $OCH_3$), 3.78 (s, 3, $OCH_3$), 2.53 (t, 2, $ArCH_2$), 2.37 (s, 3, $ArCH_3$), 2.16 (t, 2, $CH_2$); Anal. ($C_{27}H_{27}NO_3$) C, H, N.

Trans-2-methyl-6-benzyl-10,11-dimethoxy-5,6,6a,7,8,12b-hexahydro-benzo[a]phenanthridine-5-one. A solution of 4.80 g (11.62 mmol) of the 6,7-dimethoxy enamide prepared above, in 500 ml of THF, was introduced to an Ace Glass 500 ml photochemical reactor. This solution was stirred while irradiating for 2 hours with a 450 watt Hanovia medium pressure, quartz, mercury-vapor lamp seated in a water cooled, quartz immersion well. The solution was concentrated in vacuo and crystallized from diethyl ether to provide 2.433 (50.7%) of the 10,11-dimethoxy lactam, mp 183°-195° C. CIMS (isobutane); M+1 414; $^1$H-NMR ($CDCl_3$); δ8.13 (d, 1, ArH), 7.30 (s, 1, ArH), 7.23 (m, 6, ArH), 6.93 (s, 1, ArH), 6.63 (s, 1, ArH), 5.38 (d, 1, $ArCH_2N$), 5.30 (d, 1, $ArCH_2N$), 4.34 (d, 1, $Ar_2CH$, J=11.4 Hz), 3.89 (s, 3, $OCH_3$), 3.88 (s, 3, $OCH_3$), 3.76 (m, 1, CHN), 2.68 (m, 2, $ArCH_2$), 2.37 (s, 3, $ArCH_3$), 2.25 (m, 1, $CH_2CN$), 1.75 (m, 1, $CH_2CN$); Anal. ($C_{27}H_{27}NO_3$) C, H, N.

Trans-2-methyl-6-benzyl-10,11-dimethoxy-5,6,6a,7,8,12b-hexahydrobenzo[a]phenanthridinehydrochloride. A solution of 1.349 g (3.27 mmol) of the lactam prepared above, in 100 ml dry THF was cooled in an ice-salt bath and 4.0 equiv. (13.0 ml) of 1.0 molar $BH_3$ was added via syringe. The reaction was heated as reflux under nitrogen overnight. Methanol (10 ml) was added dropwise to the reaction mixture and reflux was continued for 1 hour. The solvent was removed by rotary vacuum evaporation. The residue was chased two times with methanol and twice with ethanol. The flask was placed under high vacuum (0.05 mm Hg) overnight. The residue was dissolved in ethanol and was carefully acidified with concentrated HCl. The violatiles were removed and the product was crystallized from ethanol to afford 1.123 g (78.9%) of the hydrochloride salt, mp 220°-223° C. CIMS (isobutane); M+1 400; $^1$H-NMR ($CDCl_3$, free base); δ7.37 (d, 2, ArH), 7.33 (m, 2, ArH), 7.26 (m, 1, ArH), 7.22 (s, 1, ArH), 7.02 (d, 1, ArH), 6.98 (d, 1, ArH), 6.89 (s, 1, ArH), 6.72 (s, 1, ArH), 4.02 (d, 1, $Ar_2CH$, J=10.81 Hz), 3.88 (s, 3, OCH$_3$), 3.86 (d, 1, ArCH$_2$N), 3.82 (m, 1, ArCH$_2$N), 3.78 (s, 3, OCH$_3$), 3.50 (d, 1, ArCH$_2$N), 3.30 (d, 1, ArCH$_2$N), 2.87 (m, 1, ArCH$_2$), 2.82 (m, 1, CHN), 2.34 (m, 1, CH$_2$CN), 2.32 (s, 3, ArCH$_3$), 2.20 (m, 1, ArCH$_2$), 1.93 (m, 1, CH$_2$CN); Anal. (C$_{27}$H$_{29}$NO$_2$C, H, N.

Trans-2-methyl-10,11-dimethoxy-5,6,6a,7,8,12b-hexahydrobenzo[a]phenanthridine hydrochloride. A solution of 0.760 g (1.75 mmol) of the 6-benzyl hydrochloride salt prepared above in 100 ml of 95% ethanol containing 150 mg of 10% Pd/C catalyst was shaken at room temperature under 50 psig of H$_2$ for 8 hours. After removal of the catalyst by filtration through Celite, the solution was concentrated to dryness under vacuum and the residue was recrystallized from acetonitrile to afford 0.520 g (86.2%) of the crystalline salt, mp 238°–239° C. CIMS (isobutane); M+1 310; $^1$H-NMR (DMSO, HCl SALT); δ10.04 (s, 1, NH), 7.29 (d, 1, ArH), 7.16 (m, 2, ArH), 6.88 (s, 1, ArH), 6.84 (s, 1, ArH), 4.31 (s, 2, ArCH$_2$N), 4.23 (d, 1, Ar$_2$CH, J=10.8 Hz), 3.76 (s, 3, OCH$_3$), 3.70 (s, 3, OCH$_3$), 2.91 (m, 2, ArCH$_2$), 2.80 (m, 1, CHN), 2.49 (s, 3, ArCH$_3$), 2.30 (m, 1, CH$_2$CN), 2.09 (m, 1, CH$_2$CN); Anal. (C$_{20}$H$_{23}$NO$_2$) C, H, N.

Trans-2-methyl-10,11-dihydroxy-5,6,6a,7,8,12b-hexahydrobenzo[a]phenanthridinehydrochloride. 0.394 g (1.140 mmol) of the O,O-dimethyl hydrochloride salt prepared above was converted to its free base. The free base was dissolved in 35 ml of dichloromethane and the solution was cooled to −78° C., 4.0 equiv. (4.56 ml) of a 1.0 molar solution of BBr$_3$ was added slowly via syringe. The reaction was stirred under N$_2$ overnight with concomitant warming to room temperature. 7.0 ml of methanol was added to the reaction mixture and the solvent was removed by rotary vacuum evaporation. The flask was placed under high vacuum (0.05 mm Hg) overnight. The residue was dissolved in water and was carefully neutralized to its free base initially with sodium bicarbonate and finally with ammonium hydroxide (1–2 drops). The free base was isolated by suction filtration and was washed with cold water. The filtrate was extracted several times with dichloromethane and the organic extacts were dried, filtered and concentrated. The filter cake and the organic residue were combined, dissolved in ethanol and carefully acidified with concentrated HCl. After removal of the volatiles, the HCl salt was crystallized as a solvate from methanol in a yield of 0. 185 g (51%), mp (decomposes @ 190° C). CIMS (isobutane); M+1 282; $^1$H-NMR (DMSO, HCl salt); δ9.52 (s, 1, NH), 8.87 (d, 2, OH), 7.27 (d, 1, ArH), 7.20 (s, 1, ArH), 7.15 (d, 1, ArH), 6.72 (s, 1, ArH), 6.60 (s, 1, ArH), 4.32 (s, 2, ArCH$_2$N), 4.10 (d, 1, ArCH$_2$CH, J=11.26 Hz), 2.90 (m, 1, CHN), 2.70 (m, 2, ArCH$_2$), 2.32 (s, 3, ArCH$_3$), 2.13 (m, 1, CH$_2$CN), 1.88 (m, 1, CH$_2$CN); Anal. (C$_{18}$H$_{19}$NO$_2$) C, H, N.

EXAMPLE 2

2-(N-benzyl-N-3-methylbenzoyl)-6,7-dimethoxy-3,4-dihydro-2-naphthylamine. To a solution of 3.504 g (17.0 mmol) of 6,7-dimethoxy-β-tetralone in 100 ml of toluene was added 1.870 g (1.025 equiv.) of benzylamine. The reaction was heated at reflux overnight under N$_2$ with continuous water removal. The reaction was cooled and the solvent was removed by rotary vacuum evaporation to yield the crude N-benzyl enamine as a brown oil.

Meanwhile, the 3-methylbenzoyl chloride acylating agent was prepared by suspending 3.016 g (22.0 mmol) of m-toluic acid in 100 ml benzene. To this solution was added 2.0 equiv. (3.84 ml) of oxalyl chloride, dropwise via a pressure-equalizing dropping funnel at 0° C. DMF (2–3 drops) was added to the reaction mixture catalytically and the ice bath was removed. The progress of the reaction was monitored via infrared spectroscopy. The solvent was removed by rotary vacuum evaporation and the residual oil was pumped down under high vacuum overnight.

The crude N-benzyl enamine residue was dissolved in 100 ml of CH$_2$Cl$_2$, and to this solution was added 1.763 g (17.42 mmol) of triethylamine at 0° C. 3-methylbenzoyl chloride (2.759 g, 17.84 mmol) was dissolved in 20 ml CH$_2$Cl$_2$ and this solution was added dropwise to the cold, stirring N-benzyl enamine solution. The reaction was allowed to warm to room temperature and was left to stir under N$_2$ overnight. The reaction mixture was washed successively with 2×30 ml of 5% aqueous HCl, 2× 30 ml of saturated sodium bicarbonate solution, saturated NaCl solution, and was dried over MgSO$_4$. After filtration, the filtrate was concentrated under vacuum. Crystallization from diethyl ether gave 4.431 g (63.1%) of the enamide mp 96°–97° C. CIMS (isobutane); M+1 414; $^1$H-NMR (CDCl$_3$); δ7.36 (s, 1, ArH), 7.26 (m, 3, ArH), 7.20 (m, 5, ArH), 6.50 (s, 1, ArH), 6.40 (s, 1, ArH), 6.05 (s, 1, ArCH), 4.95 (s, 2, ArCH$_2$N), 3.75 (s, 3, OCH$_3$), 3.74 (s, 3, OCH$_3$), 2.43 (t, 2, ArCH$_2$), 2.28 (s, 3, ArCH$_3$), 2.07 (t, 2, CH$_2$) Anal. (C$_{27}$H$_{27}$NO$_3$) C, H, N, Trans-3-methyl-6-benzyl-10,11-dimethoxy-5,6,6a,7,8,12b-hexahydrobenzo[a]phenanthridine-5-one. A solution of 1.922 g (4.65 mmol) of the 6,7-dimethoxy enamide prepared above, in 500 ml of THF, was introduced to an Ace Glass 500 ml photochemical reactor. This solution was stirred while irradiating for 5 hours with a 450 watt Hanovia medium pressure, quartz, mercury-vapor lamp seated in a water cooled, quartz immersion well. The solution was concentrated in vacuo and crystallized from diethyl ether to provide 0.835 g (43.4%) of the 10, 11dimethoxy lactam, mp 154°–157° C. CIMS (isobutane); M+1 414; $^1$H-NMR (CDCl$_3$); δ7.94 (S, 1, ArH), 7.34 (d, 1, ArH), 7.17 (m, 6, ArH), 6.84 (s, 1, ArH), 6.54 (s, 1, ArH), 5.28 (d, 1, ArCH$_2$N), 4.66 (d, 1, ArCH$_2$N), 4.23 (d, 1, Ar$_2$CH, J=11.4 Hz), 3.78 (s, 3, OCH$_3$), 3.74 (s, 3, OCH$_3$), 3.61 (m, 1, CHN), 2.59 (m, 2, ArCH$_2$), 2.34 (s, 3, ArCH$_3$), 2.15 (m, 1, CH$_2$CN), 1.63 (m, 1, CH$_2$CN); Anal. (C$_{27}$H$_{27}$NO$_3$) C, H, N.

Trans-3-methyl-6-benzyl-10,11-dimethoxy-5,6,6a,7,8,12b-hexahydrobenzo[a]phenanthridinehydrochloride. A solution of 0.773 g (1.872 mmol) of the lactam prepared above, in 50 ml dry THF was cooled in an ice-salt bath and 4.0 equiv. (7.5 ml) of 1.0 molar BH$_3$ was added via syringe. The reaction was heated as reflux under nitrogen overnight. Methanol (6 ml) was added dropwise to the reaction mixture and reflux was continued for 1 hour. The solvent was removed by rotary vacuum evaporation. The residue was chased two times with methanol and twice with ethanol. The flask was placed under high vacuum (0.05 mm Hg) overnight. The residue was dissolved in ethanol and was carefully acidified with concentrated HCl. The violatiles were removed and the product was crystallized from ethanol to afford 0.652 g (80%) of the hydrochloride salt, mp 193°–195° C. CIMS (isobutane); M+1 400; $^1$H-NMR (CDCl$_3$, free base); δ7.38 (d, 2, ArH), 7.33 (m, 2, ArH), 7.28 (m, 2, ArH), 7.07 (d, 1, ArH), 6.90 (s, 1, ArH), 6.88 (s, 1, ArH), 6.72 (s, 1, ArH), 4.02 (d, 1, Ar$_2$CH, J=11.2 Hz), 3.90 (d, 1, ArCH$_2$N), 3.87 (s, 3, OCH$_3$), 3.82 (m, 1, ArCH$_2$N), 3.78 (s, 3, OCH$_3$), 3.48 (d, 1, ArCH$_2$N), 3.30 (d, 1, ArCH$_2$N), 2.88 (m, 1, ArCH$_2$), 2.82 (m, 1, CHN), 2.36 (m, 1, CH$_2$CN), 2.32 (s, 3, ArCH$_3$), 2.20 (m, 1, ArCH$_2$), 1.95 (m, 1, CH$_2$CN); Anal. (C$_{27}$H$_{29}$NO$_2$) C, H, Trans-3-methyl-10,11-dimethoxy-5,6,6a, 7,8,12b-hexahydrobenzo[a]phenanthridine hydrochloride. A solution of 0.643 g (1.47 mmol) of the 6-benzyl hydrochloride salt prepared above in 100 ml of 95 % ethanol containing 130 mg of 10% Pd/C catalyst was shaken at room temperature under 50 psig of H$_2$ for 8 hours. After removal of the catalyst by filtration through Celite, the solution was concentrated to dryness under vacuum and the residue was recrystallized from acetonitrile to afford 0.397 g (78%) of the crystalline salt, mp 254°–256° C. CIMS (isobutane); M+1 310; $^1$H-NMR (DMSO, HCl SALT); δ10.01 (s, 1, NH), 7.36 (d, 1, ArH), 7.09 (d, 1, ArH), 6.98 (s, 1, ArH), 6.92 (s, 1, ArH), 6.74 (s, 1, ArH), 4.04 (s, 2, ArCH$_2$N), 3.88 (s, 3, OCH$_3$), 3.81 (s, 3, OCH$_3$), 3.76 (d, 1, Ar$_2$CH), 2.89 (m, 2, ArCH$_2$), 2.70 (m, 1, CHN), 2.36 (s, 3, ArCH$_3$), 2.16 (m, 1, CH$_2$CN), 1.70 (m, 1, CH$_2$CN); Anal. (C$_{20}$H$_{23}$NO$_2$) C, H, N.

Trans-3-methyl-10,11 -dihydroxy-5,6,6a,7,8,12b-hexahydrobenzo[a]phenanthridine hydrochloride. 0.520 g (1.51 mmol) of the O,O-dimethyl hydrochloride salt prepared above was converted to its free base. The free base was dissolved in 35 ml of dichloromethane and the solution was cooled to −78° C. 4.0 equiv. (6.52 ml) of a 1.0 molar solution of BBr$_3$ was added slowly via syringe. The reaction was stirred under N$_2$ overnight with concomitant warming to room temperature. 7.0 ml of methanol was added to the reaction mixture and the solvent was removed by rotary vacuum evaporation. The flask was placed under high vacuum (0.05 mm Hg) overnight. The residue was dissolved in water and was carefully neutralized to its free base initially with sodium bicarbonate and finally with ammonium hydroxide (1–2 drops). The free base was isolated by suction filtration and was washed with cold water. The filtrate was extracted several times with dichloromethane and the organic exacts were dried, filtered and concentrated. The filter cake and the organic residue were combined, dissolved in ethanol and carefully acidified with concentrated HCl. After removal of the volatiles, the HCl salt was crystallized as a solvate from methanol in a yield of 0.341 g (71.3%), mp (decomposes @ 190° C). CIMS (isobutane); M+1 282; $^1$H-NMR (DMSO, HCl salt); δ9.55 (s, 1, NH), 8.85 (d, 2, OH), 7.30 (d, 1, ArH), 7.22 (s, 1, ArH), 7.20 (d, 1, ArH), 6.68 (s, 1, ArH), 6.60 (s, 1, ArH), 4.31 (s, 2, ArCH$_2$N), 4.09 (d, 1, ArCH$_2$CH, J=11.2 Hz), 2.91 (m, 1, CHN), 2.72 (m, 2, ArCH$_2$), 2.35 (s, 3, ArCH$_3$), 2.16 (m, 1, CH$_2$CN, 1.85 (m, 1, CH$_2$CN); Anal. (C$_{18}$H$_{19}$NO$_2$) C, H, N.

EXAMPLE 3

2-(N-benzyl-N-3-methylbenzoyl)-6,7-dimethoxy-3,4-dihydro-2-naphthylamine. To a solution of 5.123 g (24.8 mmol) of 6,7-dimethoxy-β-tetralone in 200 ml of toluene was added 2.929 g (1.025 equiv.) of benzylamine. The reaction was heated at reflux overnight under N$_2$ with continuous water removal. The reaction was cooled and the solvent was removed by rotary vacuum evaporation to yield the crude N-benzyl enamine as a brown oil.

Meanwhile, the 2-methylbenzoyl chloride acylating agent was prepared by suspending 4.750 g (42.2 mmol) of o-toluic acid in 100 ml benzene. To this solution was added 2.0 equiv. (7.37 ml) of oxalyl chloride, dropwise via a pressure-equalizing dropping funnel at 0° C. DMF (2–3 drops) was added to the reaction mixture catalytically and the ice bath was removed. The progress of the reaction was monitored via infrared spectroscopy. The solvent was removed by rotary vacuum evaporation and the residual oil was pumped down under high vacuum overnight.

The crude N-benzyl enamine residue was dissolved in 100 ml of CH$_2$Cl$_2$, and to this solution was added 2.765 g (1.1 equiv.) of triethylamine at O° C. 4-methylbenzoyl chloride (4.226 g, 27.3 mmol) was dissolved in 25 ml CH$_2$Cl$_2$ and this solution was added dropwise to the cold, stirring N-benzyl enamine solution. The reaction was allowed to warm to room temperature and was left to stir under N$_2$ overnight. The reaction mixture was washed successively with 2×30 ml of 5% aqueous HCl, 2×30 ml of saturated sodium bicarbonate solution, saturated NaCl solution, and was dried over MgSO$_4$. After filtration, the filtrate was concentrated under vacuum. The resulting oil was purified via the chromatotron utilizing a 5% ether/dichloromethane eluent mobile phase to yield 3.950 g (38.5%) of the pure oil. CIMS (isobutane); M+1 414; $^1$H-NMR (CDCl$_3$); δ7.34 (d, 2, ArH), 7.30 (m, 2, ArH), 7.25 (d, 2, ArH), 7.14 (m, 2, ArH), 7.07 (m, 1, ArH), 6.47 (s, 1, ArH), 6.37 (s, 1, ArH), 6.04 (s, 1, ArCH), 4.96 (s, 2, ArCH$_2$N), 3.78 (s, 3, OCH$_3$), 3.77 (s, 3, OCH$_3$), 2.39 (s, 3, ArCH$_3$), 2.30 (t, 2, ArCH$_2$), 1.94 (t, 2, CH$_2$), Trans-4-methyl-6-benzyl-10,11-dimethoxy-5,6,6a,7,8,12b-hexahydrobenzo[a]phenanthridine-5-one. A solution of 2.641 g (6.395 mmol) of the 6,7-dimethoxy enamide prepared above, in 450 ml of THF, was introduced to an Ace Glass 500 ml photochemical reactor. This solution was stirred while irradiating for 3 hours with a 450 watt Hanovia medium pressure, quartz, mercury-vapor lamp seated in a water cooled, quartz immersion well. The solution was concentrated in vacuo and crystallized from diethyl ether to provide 0.368 (20%) of the 10,11-dimethoxy lactam, mp 175°–176° C. CIMS (isobutane); M+1 414; $^1$H-NMR (CDCl$_3$); δ7.88 (m, 3, ArH), 7.65 (d, 1, ArH), 7.40 (m, 2, ArH), 7.21 (m, 2, ArH), 6.87 (s, 1, ArH), 6.60 (s, 1, ArH), 5.34 (d, 1, ArCH$_2$N), 4.72 (d, 1, ArCH$_2$N), 4.24 (d, 1, Ar$_2$CH, J=10.9 Hz), 3.86 (s, 3, OCH$_3$), 3.85 (s, 3, OCH$_3$), 3.68 (m, 1, CHN), 2.73 (s, 3, ArCH$_3$), 2.64 (m, 2, ArCH$_2$); 2.20 (m, 1, CH$_2$CN), 1.72 (m, 1, CH$_2$CN).

Trans-4-methyl-6-benzyl-10,11-dimethoxy-5,6,6a, 7,8,12b-hexahydrobenzo[a]phenanthridinehydrochloride. A solution of 1.640 g (3.97 mmol) of the lactam prepared above, in 100 ml dry THF was cooled in an ice-salt bath and 4.0 equiv. (15.9 ml) of 1.0 molar BH$_3$ was added via syringe. The reaction was heated as reflux under nitrogen overnight. Methanol (10 ml) was added dropwise to the reaction mixture and reflux was continued for 1 hour. The solvent was removed by rotary vacuum evaporation. The residue was chased two times with methanol and twice with ethanol. The flask was placed under high vacuum (0.05 mm Hg) overnight. The residue was dissolved in ethanol and was carefully acidified with concentrated HCl. The violatiles were removed and the product was crystallized from ethanol to afford 1.288 g (74.5%) of the hydrochloride salt, mp 232°–235° C. CIMS (isobutane); M+1, 400; $^1$H-NMR (CDCl$_3$, free base); δ7.38 (d, 2, ArH), 7.33 (m, 2, ArH), 7.27 (d, 1, ArH), 7.24 (m, 1, ArH), 7.16 (m, 1, ArH), 7.06 (d, 1, ArH), 6.85 (s, 1, ArH), 6.71 (s, 1, ArH), 4.05 (d, 1, Ar$_2$CH, J=10.8 Hz), 3.89 (d, 1, ArCH$_2$N), 3.87 (s, 3, OCH$_3$), 3.82 (m, 1, ArCH$_2$N), 3.76 (s, 3, OCH$_3$), 3.55 (d, 1, ArCH$_2$N), 3.31 (d, 1, ArCH$_2$N), 2.88 (m, 1, ArCH$_2$), 2.81 (m, 1, CHN), 2.34 (m, 1, CH$_2$CN), 2.20 (m, 1, ArCH$_2$), 2.17 (s, 3, ArCH$_3$), 1.94 (m, 1, CH$_2$CN).

Trans-4-methyl-10,11-dimethoxy-5,6,6a,7,8,12b-hexahydrobenzo[a]phenanthridine hydrochloride. A solution of 0.401 g (0.92 mmol) of the 6-benzyl hydrochloride salt prepared above in 100 ml of 95% ethanol containing 100 mg of 10% Pd/C catalyst was shaken at room temperature under 50 psig of H$_2$ for 8 hours. After removal of the catalyst by filtration through Celite, the solution was concentrated to dryness under vacuum and the residue was recrystallized from acetonitrile to afford 0.287 g (90.2%) of the crystalline salt, mp 215°–216° C. CIMS (isobutane); M+1 310; $^1$H-NMR (CDCl$_3$, free base); δ9.75 (s, 1, NH), 7.29 (d, 1, ArH), 7.28 (d, 1, ArH), 7.21 (m, 1, ArH), 6.86 (s, 1, ArH), 6.81 (s, 1, ArH), 4.35 (d, 1, ArCH$_2$N), 4.26 (d, 1, ArCH$_2$N), 4.23 (d, 1, Ar$_2$CH, J=11.17 Hz), 3.75 (s, 3, OCH$_3$), 3.65 (s, 3, OCH$_3$), 2.96 (m, 1, CHN), 2.83 (m, 2, ArCH$_2$), 2.30 (s, 3, ArCH$_3$), 2.21 (m, 1, CH$_2$CN), 1.93 (m, 1, CH$_2$CN).

Trans-4-methyl-10,11-dihydroxy-5,6,6a, 7,8,12b-hexahydrobenzo[a]phenanthridine hydrochloride. 0.485 g (1.40 mmol) of the O,O-dimethyl hydrochloride salt prepared above was converted to its free base. The free base was dissolved in 35 ml of dichloromethane and the solution was cooled to −78° C. 4.0 equiv. (5.52 ml) of a 1.0 molar solution of BBr$_3$ was added slowly via syringe. The reaction was stirred under N$_2$ overnight with concomitant warming to room temperature. 7.0 ml of methanol was added to the reaction mixture and the solvent was removed by rotary vacuum evaporation. The flask was placed under high vacuum (0.05 mm Hg) overnight. The residue was dissolved in water and was carefully neutralized to its free base initially with sodium bicarbonate and finally with ammonium hydroxide (1–2 drops). The free base was isolated by suction filtration and was washed with cold water. The filtrate was extracted several times with dichloromethane and the organic extacts were dried, filtered and concentrated. The filter cake and the organic residue were combined, dissolved in ethanol and carefully acidified with concentrated HCl. After removal of the volatiles, the HCl salt was crystallized as a solvate from methanol in a yield of 0.364 g (81.6%), mp (decomposes @ 195° C.). CIMS (isobutane); M+1 282; $^1$H-NMR (DMSO, HCl salt); d 9.55 (s, 1, NH), 8.85 (s, 1, OH), 8.80 (s, 1, OH), 7.28 (m, 2, ArH), 7.20 (d, 1, ArH), 6.65 (s, 1, ArH), 6.60 (s, 1, ArH), 4.32 (d, 1, ArCH$_2$N), 4.26 (d, 1, ArCH$_2$N), 4.13 (d, 1, Ar$_2$CH, J=11.63 Hz), 2.92 (m, 1, CHN), 2.75 (m, 1, ArCH$_2$), 2.68 (m, 1, ArCH$_2$), 2.29 (s, 3, ArCH$_3$), 2.17 (m, 1, CH$_2$CN), 1.87 (m, 1, CH$_2$CN). Using the same procedures described in Examples 1–3 above, and those described in U.S. Pat. No. 5,047,536, the compounds of Examples 4–35 as set forth in Table I below are synthesized.

TABLE I

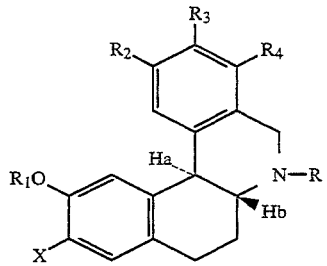

| EXAMPLE NUMBER | R | R$_1$ | R$_2$ | R$_3$ | R$_4$ | X |
|---|---|---|---|---|---|---|
| 1 | H | H | CH$_3$ | H | H | OH |
| 2 | H | H | H | CH$_3$ | H | OH |
| 3 | H | H | H | H | CH$_3$ | OH |
| 4 | H | H | C$_6$H$_5$ | H | H | OH |
| 5 | CH$_3$ | H | CH$_3$ | H | H | OH |
| 6 | C$_3$H$_7$ | H | H | CH$_3$ | H | OH |
| 7 | H | H | C$_2$H$_5$ | H | H | OH |
| 8 | H | H | H | C$_2$H$_5$ | H | OH |
| 9 | H | H | H | CH$_3$ | CH$_3$ | Br |
| 10 | C$_3$H$_7$ | H | CH$_3$ | CH$_3$ | H | OH |
| 11 | C$_2$H$_5$ | H | H | CH$_3$ | CH$_3$ | Br |
| 12 | CH$_3$ | H | H | H | C$_2$H$_5$ | OH |
| 13 | C$_4$H$_9$ | H | H | OH | H | OH |
| 14 | H | H | CH$_3$ | OH | H | OH |
| 15 | H | H | H | F | H | OH |
| 16 | H | H | OH | H | H | Br |
| 17 | H | H | Br | H | H | OH |
| 18 | H | CH$_3$ | H | Br | H | OCH$_3$ |
| 19 | H | CH$_3$ | H | H | Br | OCH$_3$ |
| 20 | H | CH$_3$ | CH$_3$ | Br | H | OCH$_3$ |
| 21 | CH$_3$ | H | F | H | H | OH |
| 22 | CH$_3$ | H | H | F | H | OH |
| 23 | CH$_3$ | H | H | H | F | OH |
| 24 | C$_2$H$_5$ | H | H | OH | H | F |
| 25 | C$_2$H$_5$ | H | CH$_3$ | OH | H | F |
| 26 | C$_2$H$_5$ | H | CH$_3$O | H | CH$_3$ | F |
| 27 | C$_3$H$_7$ | H | H | CH$_3$O | H | Cl |
| 28 | C$_3$H$_7$ | H | H | CH$_3$ | CH$_3$O | Cl |
| 29 | C$_3$H$_7$ | H | C$_2$H$_5$O | H | H | OH |
| 30 | C$_3$H$_7$ | H | H | OH | H | OH |
| 31 | C$_4$H$_9$ | H | CH$_3$ | H | H | OH |
| 32 | C$_4$H$_9$ | H | H | OH | CH$_3$ | OH |
| 33 | C$_4$H$_9$ | H | OH | Cl | H | OH |
| 34 | C$_4$H$_9$ | H | OH | Cl | H | OH |
| 35 | C$_4$H$_9$ | H | H | CH$_3$ | H | I |

The affinity for the compounds of Examples 1, 2 and 4 for D-1 and D-2 binding sites was assayed utilizing rat brain striatal homogenates having D-1 and D-2 binding sites labeled with $^3$H-SCH 23390 and 3H-spiperone, respectively. The data obtained in that assay for dihydrexidine and the compounds of Examples 1, 2 and 4 are reported in Table II.

TABLE II

| Example | D-1 Affinity | D-2 Affinity | D-1:D-2 Selectivity |
|---|---|---|---|
| 1 | 14 nM | 650 nM | 46 |
| 2 | 7 nM | 45 nM | 6 |
| 4 | 290 nM | 185 nM | 0.6 |
| Dihydrexidine | 8 nM | 100 nM | 13 |

The compounds of this invention can be formulated in conventional drug dosage forms. Preferred doses of the present compounds depend on many factors, including the indication being treated, the route of administration, and the overall condition of the patient. For oral administration, for example, effective doses of the present compounds are expected to range from about 0.1 to about 50 mg/kg, more typically about 0.5 to about 25 mg/kg. Effective parenteral doses can range from about 0.01 to about 15 mg/kg of body weight, more typically from about 0.1 to about 5 mg/kg of body weight. In general, treatment regimens utilizing compounds in accordance with the present invention comprise administration of from about 1 mg to about 500 mg of the compounds of this invention per day in multiple doses or in a single dose.

Liquid dosage forms for oral administration may include pharmaceutically acceptable emulsions, microemulsions, solutions, suspensions, and syrups containing inert diluents commonly used in the art, such as water. Such compositions may also comprise adjuvants such as wetting agents, emulsifying and suspending agents, sweetening, and flavoring agents. Injectable preparations of the compounds of the present invention can be formulated utilizing art-recognized procedures by dispersing or dissolving an effective dose of the compound in a parenterally acceptable diluent such as water, or more preferably isotonic sodium chloride solution. The parenteral formulations can be sterilized using art-recognized microfiltration techniques.

The compounds of this invention can also be formulated as solid dosage forms for oral administration such as capsules, tablets, powders, pills and the like. Typically the active compound is admixed with an inert diluent or carrier such as sugar or starch and other excipients appropriate for the dosage form. Thus tabletting formulations will include acceptable lubricants, binders and/or disintegrants. Optionally powder compositions comprising an active compound of this invention and, for example, a starch or sugar carrier can be filled into gelatin capsules for oral administration. Other dosage forms of the compounds of the present invention can be formulated using art-recognized techniques in forms adapted for the specific mode of administration.

The foregoing examples are illustrative of the invention and are not intended to limit the invention to the disclosed compounds. Variations and modifications of the exemplified compounds obvious to one skilled in the art are intended to be within the scope and nature of the invention as specified in the following claims.

We claim:

1. A compound of the formula

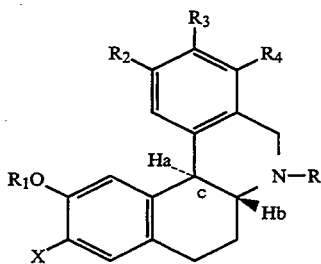

or pharmaceutically acceptable salts thereof wherein the $H_a$ and $H_b$ are trans across ring fusion bond c, R is hydrogen or $C_1$-$C_4$ alkyl $R_1$ is hydrogen or a phenoxy protecting group X is fluoro, chloro, bromo, iodo, or a group of the formula —$OR_5$ wherein $R_5$ is hydrogen or a phenoxy protecting group, and further when X is a group of the formula —$OR_5$, the groups $R_1$ and $R_5$ can be taken together to form a group of the formula —$CH_2$—; and $R_2$, $R_3$ and $R_4$ are independently selected from the group consisting of hydrogen, $C_1$-$C_4$ alkyl, phenyl, fluoro, chloro, bromo, iodo, and a group —$OR_1$ wherein $R_1$ is as defined above, provided that at least one of $R_2$, $R_3$ and $R_4$ are other than hydrogen.

2. The compound of claim 1 wherein at least one of the groups $R_2$, $R_3$, and $R_4$ is methyl.

3. The compound of claim 2 wherein X is hydroxy.

4. The compound of claim 3 wherein R is hydrogen.

5. The compound of claim 3 wherein R is $C_1$-$C_4$ alkyl.

6. The compound of claim 3 wherein R is methyl.

7. The compound of claim 3 wherein R is n-propyl.

8. The compound of claim 2 wherein X is selected from the group consisting of fluoro, chloro, bromo, or iodo.

9. The compound of claim 8 wherein X is bromo.

10. The compound of claims 9 wherein R is hydrogen.

11. The compound of claim 8 wherein R is $C_1$-$C_4$ alkyl.

12. The compound of claim 8 wherein R is methyl.

13. The compound of claim 8 wherein R is n-propyl.

14. The compound of claim 2 wherein R is hydrogen, $R_2$ is methyl, $R_3$ and $R_4$ are hydrogen, $R_1$ is hydrogen and X is hydroxy.

15. The compound of claim 2 wherein R and $R_1$ are hydrogen, X is hydroxy, $R_3$ is methyl and $R_2$ and $R_4$ are hydrogen.

16. The compound of claim 2 wherein R and $R_1$ are hydrogen, X is hydroxy, $R_4$ is methyl and $R_2$ and $R_3$ are hydrogen.

17. A method for treating a dopamine-related dysfunction of the central nervous system evidenced by an apparent neurological, psychological, physiological, or behavioral disorder, said method comprising the step of administering a compound of claim 1 in an amount effective to reduce the symptoms of said disorder.

18. A pharmaceutical composition for treating dopamine-related dysfunction of the central nervous systems characterized by an apparent neurological, physiological, psychological, or behavioral disorder, said composition consisting essentially of a therapeutically effective amount of the compound according to claim 1 and a pharmaceutically acceptable carrier thereof.

19. A method of treating a dopamine-related dysfunction of the central nervous system characterized by an apparent neurological, physiological, psychological, or behavioral disorder in a patient suffering said CNS dysfunction, said method comprising the step of administering a compound according to claim 1 exhibiting selective postsynaptic dopamine D-2 receptor affinity in an amount effective to reduce the symptoms of said disorder.

20. The method of claim 19 wherein the active compound is a compound of the formula

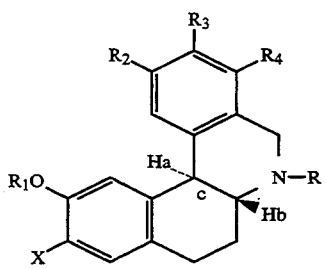

or pharmaceutically acceptable salts thereof wherein the $H_a$ and $H_b$ are trans across ring fusion bond c, R is hydrogen or $C_1$-$C_4$ alkyl $R_1$ is hydrogen or a phenoxy protecting group X is fluoro, chloro, bromo, iodo, or a group of the formula —$OR_5$ wherein $R_5$ is hydrogen or a phenoxy protecting group, and further when X is a group of the formula —$OR_5$, the groups $R_1$ and $R_5$ can be taken together to form a group of the formula —$CH_2$—; and $R_2$, $R_3$ and $R_4$ are independently selected from the group consisting of hydrogen, $C_1$-$C_4$ alkyl, phenyl, fluoro, chloro, bromo, iodo, or a group —$OR_1$ wherein $R_1$ is as defined above, provided that at least one of $R_2$, $R_3$ and $R_4$ are other than hydrogen.

* * * * *

UNITED STATES PATENT AND TRADEMARK OFFICE
CERTIFICATE OF CORRECTION

PATENT NO. : 5,420,134  
DATED : May 30, 1995  
INVENTOR(S) : David E. Nichols et al.

Page 1 of 3

It is certified that error appears in the above-indentified patent and that said Letters Patent is hereby corrected as shown below:

At column 1, line 7 please insert the following: -- This invention was made with Government support under Grant #MH-42705 awarded by the National Institute of Mental Health. The Government has certain rights in the invention.--.

In column 4, line 13 please replace "$CH_2-Cl_2$" with -- $CH_2Cl_2$ --.

In column 4, line 53 please replace "was heated as " with -- was heated at --.

In column 5, lines 5-6 please replace "$(C_{27}H_{29}NO_2$C, H, N." with --$(C_{27}H_{29}NO_2)$ C, H, N. -- .

In column 5, line 30 please replace "-78° C., 4.0 equiv." with -- -78° C. 4.0 Equiv.--.

In column 6, line 1 please replace "of m-toluic" with -- of *m*-toluic -- .

In column 6, line 29 please replace "N," with -- N. --.

UNITED STATES PATENT AND TRADEMARK OFFICE
CERTIFICATE OF CORRECTION

PATENT NO. : 5,420,134
DATED : May 30, 1995
INVENTOR(S) : David E. Nichols et al.

It is certified that error appears in the above-indentified patent and that said Letters Patent is hereby corrected as shown below:

In column 6, line 40 please replace "10, 11dimethoxy lactam" with -- 10,11-dimethoxy lactam -- .

In column 6, line 42 please replace "(S, 1, ArH)," with -- (s, 1, ArH), -- .

In column 6, line 54 please replace "The reaction was heated as" with --The reaction was heated at --.

In column 7, line 6 please replace "($C_{27}H_{29}NO_2$) C, H," with -- ($C_{27}H_{29}NO_2$) C, H, N.--.

In column 8, line 1 please replace "of o-toluic" with -- of *o*-toluic -- .

In column 8, line 30 please replace "(t, 2, $CH_2$)," with -- (t, 2, $CH_2$). --.

In column 8, line 54 please replace "The reaction was heated as" with -- The reaction was heated at --.

UNITED STATES PATENT AND TRADEMARK OFFICE
CERTIFICATE OF CORRECTION

PATENT NO. : 5,420,134
DATED : May 30, 1995
INVENTOR(S) : David E. Nichols et al.

It is certified that error appears in the above-indentified patent and that said Letters Patent is hereby corrected as shown below:

In column 9, line 47 please replace "with cold water," with -- with cold water. --.

In column 9, line 57 please replace "salt); d 9.55" with -- salt); $\delta$ 9.55 --.

Signed and Sealed this

Seventh Day of January, 1997

Attest:

BRUCE LEHMAN

Attesting Officer    Commissioner of Patents and Trademarks